US010219878B2

(12) United States Patent
Goodman et al.

(10) Patent No.: US 10,219,878 B2
(45) Date of Patent: Mar. 5, 2019

(54) DENTAL IMPLANTOPLASTY TOOL FOR PREVENTING PERI-IMPLANTIS IN DENTAL IMPLANTS

(71) Applicants: Christopher R. Goodman, Tequesta, FL (US); Alan Mark Meltzer, Voorhees, NJ (US)

(72) Inventors: Christopher R. Goodman, Tequesta, FL (US); Alan Mark Meltzer, Voorhees, NJ (US)

( * ) Notice: Subject to any disclaimer, the term of this patent is extended or adjusted under 35 U.S.C. 154(b) by 0 days.

(21) Appl. No.: 15/807,307

(22) Filed: Nov. 8, 2017

(65) Prior Publication Data

US 2018/0125615 A1 May 10, 2018

Related U.S. Application Data

(60) Provisional application No. 62/497,094, filed on Nov. 8, 2016.

(51) Int. Cl.
*A61C 8/00* (2006.01)
*B23G 9/00* (2006.01)
*A61C 17/00* (2006.01)

(52) U.S. Cl.
CPC .......... *A61C 8/0089* (2013.01); *A61C 8/0022* (2013.01); *A61C 17/00* (2013.01); *A61C 17/005* (2013.01); *B23G 9/009* (2013.01)

(58) Field of Classification Search
CPC ............... A61C 17/036; A61C 17/16
See application file for complete search history.

(56) References Cited

U.S. PATENT DOCUMENTS

| | | | |
|---|---|---|---|
| 4,899,409 A | 2/1990 | Cox, Jr. | |
| 4,941,227 A * | 7/1990 | Sussman | A46B 3/18 15/160 |
| 5,566,416 A | 10/1996 | Karls | |
| 5,782,635 A * | 7/1998 | Altvater | A61C 17/036 433/143 |
| 5,940,923 A | 8/1999 | Gunning | |
| 7,179,084 B1 * | 2/2007 | Kometas | A61C 8/0089 433/165 |
| 8,529,259 B2 * | 9/2013 | Wade | A61C 8/0089 433/142 |
| 8,739,350 B1 | 6/2014 | Lackenbauer | |
| 9,629,699 B2 * | 4/2017 | Zipprich | A61C 8/0093 |
| 9,744,011 B2 * | 8/2017 | Montana | A61C 17/036 |
| 2010/0291506 A1 * | 11/2010 | Olsson | A61C 8/0089 433/143 |
| 2013/0115570 A1 | 5/2013 | Kim | |
| 2014/0137345 A1 * | 5/2014 | Kim | A46B 9/02 15/22.1 |

(Continued)

FOREIGN PATENT DOCUMENTS

WO  WO 2013/073935 A1  5/2013

*Primary Examiner* — Ralph Lewis
(74) *Attorney, Agent, or Firm* — Nixon Peabody LLP (57) ABSTRACT

A dental tool for resurfacing thread forms of a dental implant is disclosed. The tool includes a main body having a cylindrical member with a slot. A blade having a head is inserted in the slot to orient the head to protrude from the interior surface of the cylindrical member of the main body. The main body may be rotated into traversing a thread form of the implant. A compression sleeve is inserted over the main body. The compression sleeve has an open position and a closed position to hold the blade in the slot.

14 Claims, 6 Drawing Sheets

(56) References Cited

U.S. PATENT DOCUMENTS

2015/0072308 A1* 3/2015 Kim .................... A61C 8/0089
433/165
2015/0282907 A1 10/2015 Zipprich
2017/0265968 A1* 9/2017 Brodbeck ............ A61C 8/0007

* cited by examiner

DENTAL IMPLANTOPLASTY TOOL FOR PREVENTING PERI-IMPLANTIS IN DENTAL IMPLANTS

PRIORITY CLAIM

This application claims priority to U.S. Provisional Application No. 62/497,094 filed on Nov. 8, 2016. That application and its contents are hereby incorporated by reference in its entirety.

TECHNICAL FIELD

This disclosure relates to dental implant tools and more specifically to a dental tool for resurfacing the threads of a dental implant to prevent peri-implantis.

BACKGROUND

A well-known procedure is the dental restoration of a partially or wholly edentulous patient with artificial dentition. Typically, a dental implant is seated into the bone of a patient's jaw. The exterior of the dental implant will have a series of threads that assist in seating the dental implant in the bone and hold the dental implant to the bone. The dental implant includes a socket, e.g., a bore, which is accessible through the overlying or surrounding gum tissue for receiving and supporting one or more attachments or components such as an abutment, which, in turn, are useful to fabricate and support prosthodontic restorations. The dental implant generally includes a threaded bore to receive a retaining screw for holding mating components therein. Dental implant procedures may use a variety of implanting modalities, for example, blade, threaded implant, or smooth push-in implant to attach the prosthetics.

Within the dental implant industry, there is a condition termed peri-implantitis that generally occurs and is chronic to dental implants over a period of time. This condition is brought on by bacteria and or debris attached to or attaching to the surfaces of the implant, eventually causing resorption of the surrounding bone leading to implant compromise or failure. This condition is especially prevalent to threaded implants, which are dominant within the industry market and the most difficult to clean, debride, and resurface for treatment.

Current treatment options for peri-implantitis are limited. One treatment option is scraping the implant with existing tooling. This technique yields minimal results as the thread form of an implant does not allow access to most of the debris and bacteria. This technique requires hours of chair time for a patient with questionable results. Another treatment option is the use of oral debridement chemicals. However, such chemicals cannot penetrate the bacteria's buildup and therefore also yield questionable results. Another technique is use of brushes and wire tools. Brushes and wire tools cannot provide the adequate pressures necessary to cut away the buildup also yielding unsatisfactory results.

Thus, there is a need for a dental tool that facilitates treatment of peri-implantis in dental implants. There is a further need for a dental tool that may resurface the thread forms of a dental implant. There is also a need for a dental tool that allows cleaning of a dental implant in an efficient manner.

BRIEF SUMMARY

One disclosed example is a dental tool for resurfacing thread forms of a dental implant. The tool includes a main body having a cylindrical member with a slot. A blade has a head and is inserted in the slot to orient the head to protrude from an interior surface of the cylindrical member of the main body. The main body may be rotated into traversing a thread form of the implant. A compression sleeve is inserted over the main body having an open position and a closed position to hold the blade in the slot.

Another example is a method of resurfacing the thread form of a dental implant seated in bone. A dental tool is inserted over the dental implant. The dental tool includes a main body having a cylindrical member with a slot. A blade having a head is inserted in the slot to orient the head to protrude from the interior surface of the main body. The dental tool has a compression sleeve inserted over the main body. The compression sleeve has an open position and a closed position to hold the blade in the slot. The dental tool is rotated in a first rotational direction to contact the bone. The compression sleeve is moved from the open position to the closed position. The dental tool is moved in a second rotational direction to resurface the thread form of the dental implant by contact between the head and the thread form.

The foregoing and additional aspects and implementations of the present disclosure will be apparent to those of ordinary skill in the art in view of the detailed description of various embodiments and/or aspects, which is made with reference to the drawings, a brief description of which is provided next.

BRIEF DESCRIPTION OF THE DRAWINGS

The foregoing and other advantages of the present disclosure will become apparent upon reading the following detailed description and upon reference to the drawings.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

The present examples can be embodied in many different forms. Representative embodiments are shown in the drawings, and will herein be described in detail. The present disclosure is an example or illustration of the principles of the present disclosure, and is not intended to limit the broad aspects of the disclosure to the embodiments illustrated. To that extent, elements and limitations that are disclosed, for example, in the Abstract, Summary, and Detailed Description sections, but not explicitly set forth in the claims, should not be incorporated into the claims, singly or collectively, by implication, inference, or otherwise. For purposes of the present detailed description, unless specifically disclaimed, the singular includes the plural and vice versa; and the word "including" means "including without limitation." Moreover, words of approximation, such as "about," "almost," "substantially," "approximately," and the like, can be used herein to mean "at, near, or nearly at," or "within 3-5% of," or "within acceptable manufacturing tolerances," or any logical combination thereof, for example.

Figure 1:
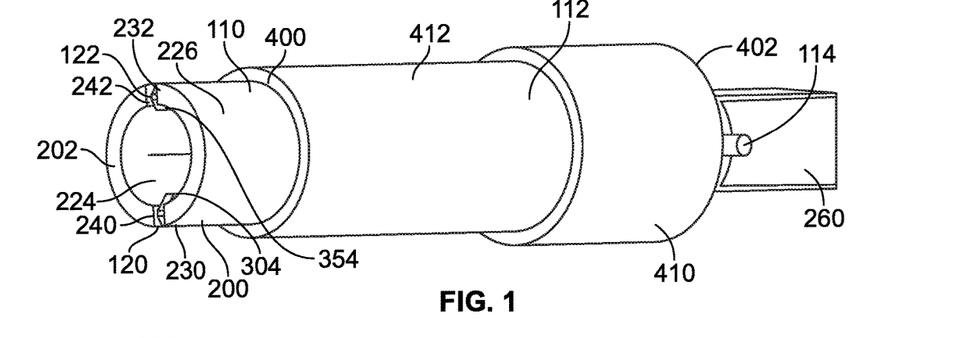
FIG. 1 is a perspective view of an example assembled example dental tool with a compression sleeve in a fully open position.
Figure 2:
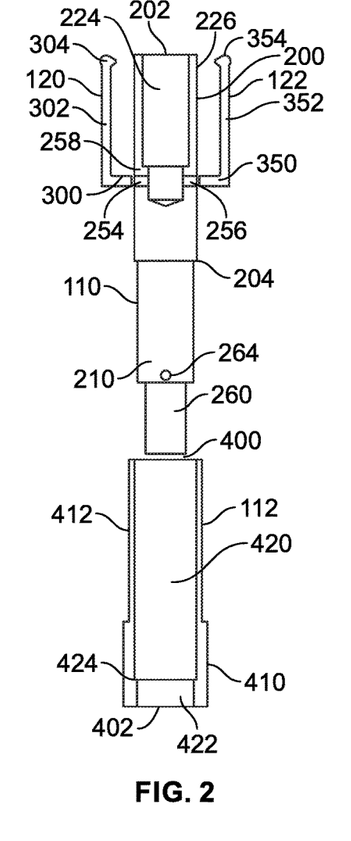
FIG. 2 is an exploded side cutaway view of the components of the example dental tool in FIG. 1.
Figure 3:
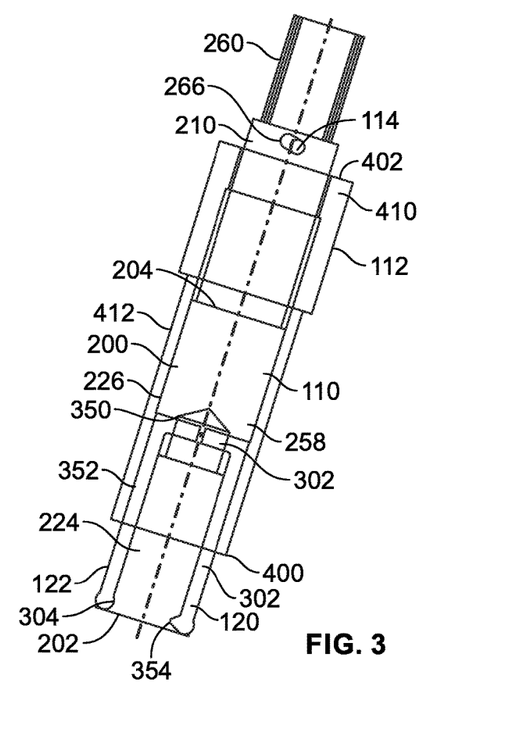
FIG. 3 is a side cutaway view of the assembly of the components of the example dental tool in FIG. 1.
Figure 4:
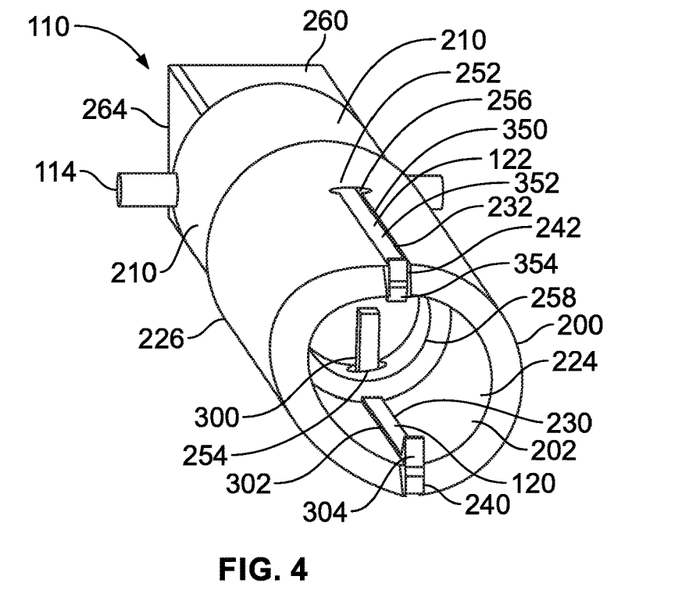
FIG. 4 is a perspective cutaway view of the assembly of the components of the example dental tool in FIG. 1.

FIG. 1 shows a perspective view of an assembled example dental tool 100. FIGS. 2-4 are different views of the different components of the dental tool 100. FIGS. 5-10 are perspective views of the individual components of the dental tool 100 in FIG. 1. FIGS. 1-10 therefore show a main body 110, a compression sleeve 112, a containment pin 114 and blades 120 and 122. The main body 110 houses the set of blades 120 and 122 that have specific geometries conforming to a specific thread form when compressed by the compression sleeve 112. The blades 120 and 122 are engaged into the thread form of a dental implant. As explained below, the blades 120 and 122 will recut affected or damaged thread surfaces of a dental implant to remove debris.

Figure 5:
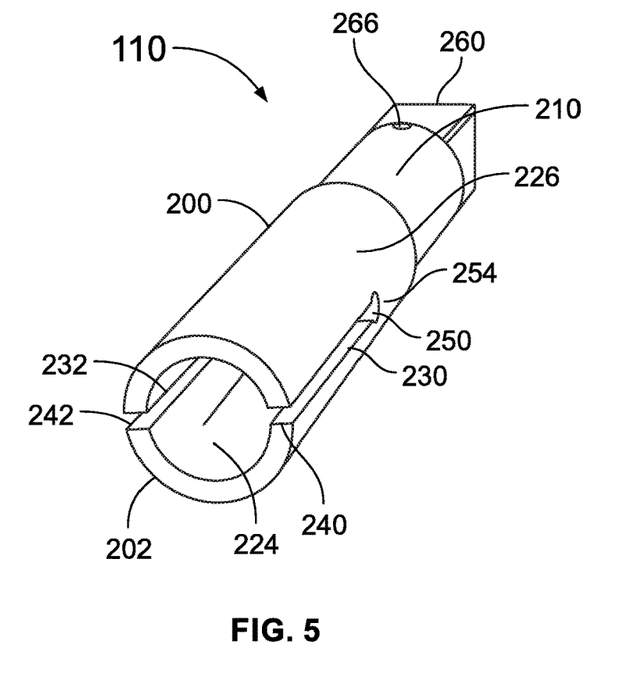
FIG. 5 is a perspective view of the main body of the dental tool in FIG. 1.
Figure 6:
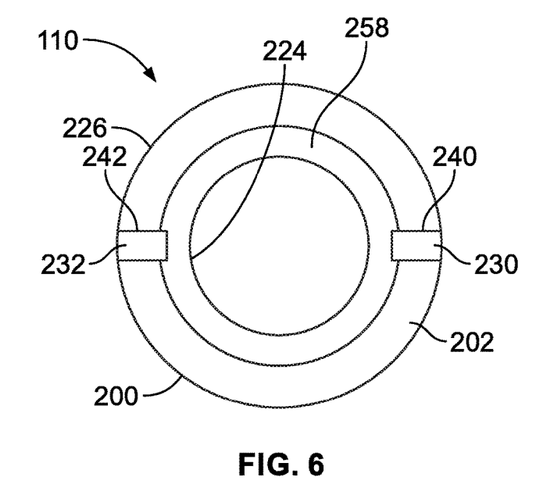
FIG. 6 is a front view of the main body of the dental tool in FIG. 1.

FIGS. 5-6 show the main body 110 of the tool 100 in FIG. 1. As shown in FIG. 6, the main body 110 holds the blades 120 and 122 to provide a counter clockwise cutting action when the main body 110 is placed over the implant and rotated.

The main body 100 includes a cylindrical socket member 200 that has an open end 202 and an opposite end 204 that is joined to one end of a support cylinder 210. The socket member 200 has an interior surface 224 and an opposite exterior surface 226 that defines two slots 230 and 232. The slots 230 and 232 are cut into the exterior surface 226 of the socket member 200. The slots 230 and 232 extend from the open end 202 to the middle of the socket member 200. Each of the slots 230 and 232 had respective open ends 240 and 242 on the open end 202 of the socket member 200. The slots 230 and 232 have respective opposite ends 250 and 252 that have respective openings 254 and 256. The interior surface 224 mounts an interior annular collar 258 that extends inwardly from the interior surface 224. The openings 254 and 256 at the respective ends 250 and 252 are wider than the slots 230 and 232. The openings 254 and 256 extend through to the interior surface 224 to accommodate the blades 120 and 122. The annular collar 258 provides support for the blades 120 and 122 when they are inserted in the slots 230 and 232.

The support cylinder 210 has a connection member 260 that protrudes from the opposite end of the support cylinder 210. The support cylinder 210 has a pair of holes 264 and 266 to the interior surface 224 for accepting the containment pin 114 that may be inserted through the holes 264 and 266 to lock in the compression sleeve 112 relative to the main body 110.

As may be seen in FIGS. 1-4, the main body 100 holds the two blades 120 and 122. The two blades 120 and 122 have respective heads protruding from the interior surface 224 of the main body 110. The blades 120 and 122 are held in place on the main body 110 by the compression sleeve 112 that is inserted over the main body 100. The compression sleeve 112 locks the blades 120 and 122 in place. The containment pin 114 holds the compression sleeve 112 in place. In this example, the main body 110 is fabricated from high temperature thermoplastic material such as RADEL. The blades 120 and 122 are fabricated from Nitinol material. The compression sleeve 112 and the containment pin 114 are fabricated from Ti-64 Eli titanium alloy. Of course any appropriate thermoplastic material may be used for the main body 110. Of course other materials such as titanium and stainless steel may be used for the compression sleeve 112, the containment pin 114 and the blades 120 and 122.

Figure 7:
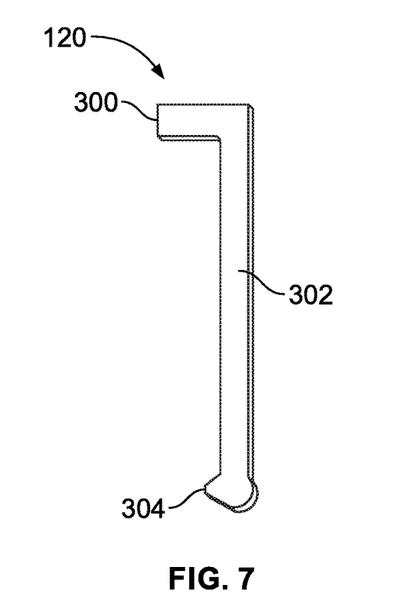
FIG. 7 is a perspective view of the blade of the dental tool in FIG. 1 for resurfacing the minor, flank and all other aspects of the thread.

FIG. 7 is a close up perspective view of the blade 120. The blade 120 includes a tab 300, a support member 302 and a head 304 opposite the tab 300. The support member 302 of the blade 120 is inserted in the slot 230 of the main body 110. The tab 300 is inserted in the opening 254 to lock the blade 120 in position in the slot 230 as shown in FIG. 4. This allows the head 304 to be oriented to protrude from interior surface 224 of the main body 110. The head 304 is shaped to allow the blade 120 to be used for resurfacing the minor, flank and all other aspects of the thread form.

Figure 8:
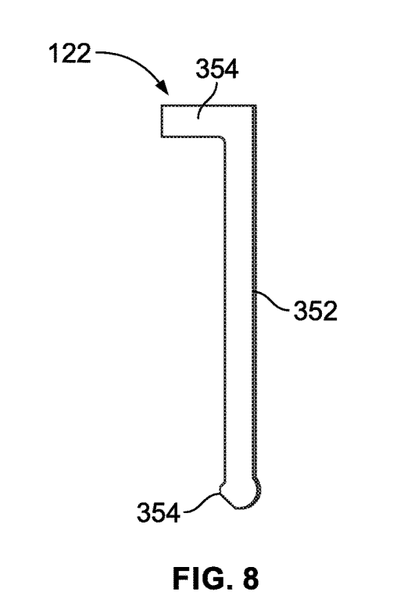
FIG. 8 is a close-up perspective view of the blade of the tool in FIG. 1 for resurfacing the major diameter of the thread.

FIG. 8 is a close up perspective view of the blade 122. The blade 122 includes a tab 350, a support member 352 and a head 354 opposite the tab 350. The support member 352 of the blade 122 is inserted in the slot 232 of the main body 110. The tab 350 is inserted in the opening 256 to lock the blade 122 in position in the slot 232. This allows the head 354 to be oriented to protrude from interior surface 224 of the main body 110. The head 354 is shaped to allow the blade 122 to be used for resurfacing the major diameter of the thread form when the main body is inserted over a dental implant.

Figure 9:
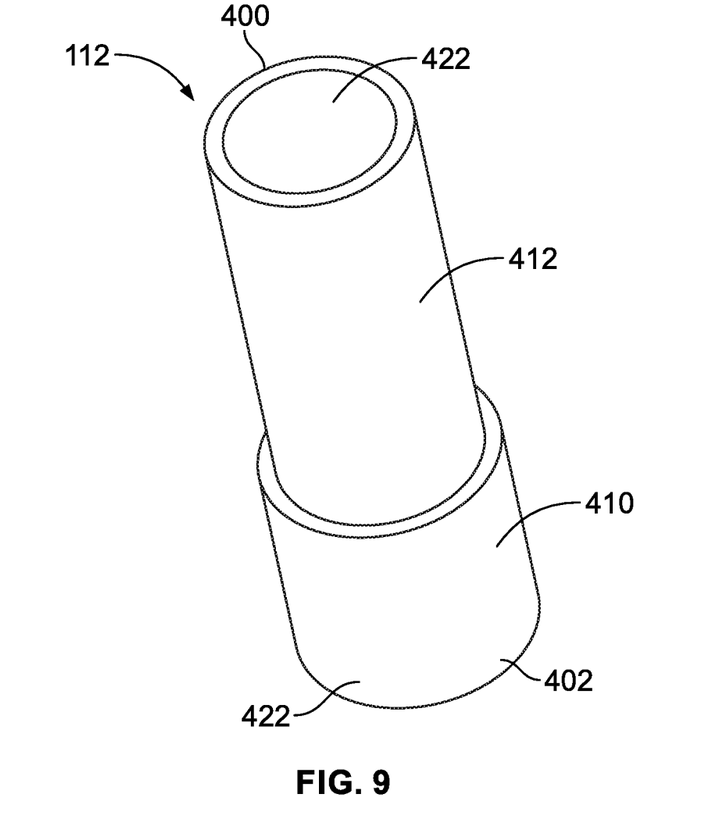
FIG. 9 is a perspective view of the compression sleeve for delivering focused compression to the blades for the tool in FIG. 1.

FIG. 9 shows the compression sleeve 112. Other views of the compression sleeve may be seen in FIGS. 2-4. The compression sleeve 112 is cylindrically shaped with opposite open ends 400 and 402 that allow the compression sleeve 112 to be slipped over the exterior surface 226 of the main body 110. The compression sleeve 112 includes a larger diameter cylinder 410 and a smaller diameter cylinder 412. The cylinders 410 and 412 form an interior bore 420 having one end at the open end 400. A smaller diameter interior bore 422 extends from the opposite open end 402. The interior bore 422 forms an annular shoulder 424 that defines the opposite end of the interior bore 420. The diameter of the interior bore 420 is a little larger than the diameter of the main body 110 to allow a snug fit when the compression sleeve 112 is telescoped over the main body 110. The open end 400 of the compression sleeve 112 is inserted over the end 204 of the support cylinder 210 and the cylindrical socket member 200. The compression sleeve 112 may be inserted over the cylindrical socket member 200. The compression sleeve 112 may move from an open position against the containment pin 114 and a closed position where the annular shoulder 424 contacts the end of the cylindrical socket member 200. When the compression sleeve 112 is inserted around the main body 110 in the closed position, it delivers focused compression to hold the blades 120 and 122 in the respective slots 230 and 232 during the use of the dental tool 100. When the main body 110 is inserted over a dental implant, the compression sleeve 112 provides rigid engagement of the heads 304 and 354 of the blades 120 and 122 to the thread path of the dental implant conforming to the pitch angle and forcing a compounding angle condition.

Figure 10:
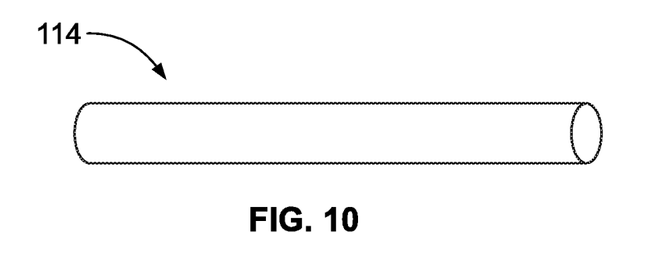
FIG. 10 is a perspective view of the containment pin of the tool in FIG. 1.

FIG. 10 shows the containment pin 114 that provides a capture and stop for the compression sleeve 112 when the containment pin 114 is inserted in the holes 264 and 266 in the support cylinder 210 as shown in FIGS. 1-4. The containment pin 114 prevents the compression sleeve 112 from sliding away from the main body 110. As explained above, when the compression sleeve 112 is in the closed position, the end 402 of the compression sleeve 112 abuts against the shoulder 424 contacting the end of the cylindrical socket member 200.

As shown in FIGS. 1-4, the blades 120 and 122 are encased within respective slots 230 and 232 of the main body 110. The blades 120 and 122 are held in place by the compression sleeve 112 in the closed position. The main body 110 is inserted over a dental implant and allows the heads 304 and 354 to engage the thread forms of the implant. The support of the slots 230 and 232 provide fixed lateral and torsional rigidity for the respective heads 304 and 354 during the cutting of the thread form of an implant. Without this rigidity, the blades 120 and 122 would only abrade or polish rather than cut into the thread form of the implant.

The connection member 260 has a square cross section in this example. The connection member 260 is designed for, but not limited to be used with a ratchet wrench commonly used in oral surgery, without the use of a centering guide interface. The ratchet wrench may be mated to the square shaped connection member 260 and allows the main body 110 to be rotated in a clockwise and counter-clockwise direction around an implant as will be explained below in reference to FIGS. 11A-11D.

The components of the dental tool 100 in FIG. 1 are assembled prior to resurfacing a dental implant. The blades 120 and 122 are inserted in the slots 230 and 232 of the main body 110. The tabs 300 and 350 of the blades 120 and 122 are inserted in the corresponding holes 254 and 256 in the main body 110 when the blades 120 and 122 are inserted in the respective slots 230 and 232. The compression sleeve 112 is placed in an open position over the main body 110 allowing the insertion of the blades 120 and 122. The compression sleeve 112 is locked in place by inserting the containment pin 114 through the holes 264 and 266 in the support cylinder 210. The compression sleeve 112 is moved to the closed position when the annular shoulder 424 contacts the cylindrical socket member 200. In the closed position, the compression sleeve 112 holds the blades 120 and 122 in place and causes the heads 304 and 354 to protrude from the interior surface 224.

Figure 11A:
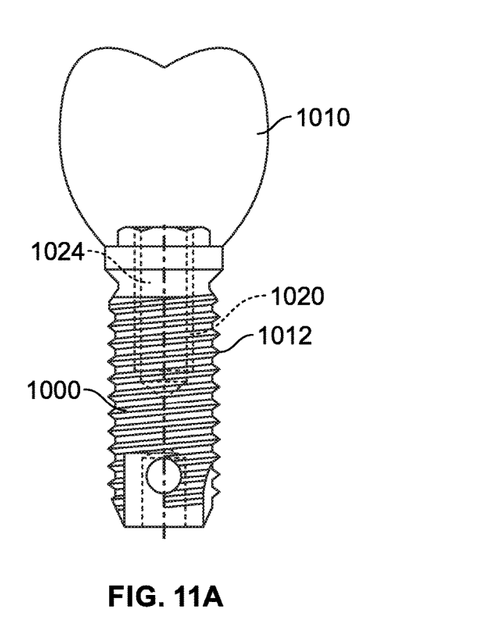
FIG. 11A-11D are views of the use of the tool in FIG. 1 to resurface a dental implant.

FIGS. 11A-11D shows the application of the assembled dental tool 100 to resurface the thread form of a dental implant 1000. FIG. 11A shows a dental assembly that includes the dental implant 1000, a retaining component and a dental mating component that in this example is a temporary abutment 1010. Other mating components may include abutments, impression copings, cover screws, monolithic prosthesis, etc. The dental implant 1000 has a roughly cylindrical body that includes a closed end and an opposite open end. The cylindrical body includes an exterior surface and an interior surface. The exterior surface has a series of threads 1012 that hold the dental implant 1000 into the bone. The implant 1000 includes an interior bore that includes the interior surface. The interior bore allows the mounting of a temporary abutment.

Typically, a temporary abutment 1010 is installed while a permanent prosthetic is prepared. When the abutment 1010 is removed, there is risk of contamination from debris accumulated on the exposed exterior threads 1012 of the implant 1000. FIG. 11A shows exterior threads 1012 of the implant 1000 that engage bone when the dental implant 1000 is inserted in a patient. The dental implant 1000 has an interior bore 1022 that holds a mounting screw 1124 that holds the temporary abutment 1010.

Figure 11B:
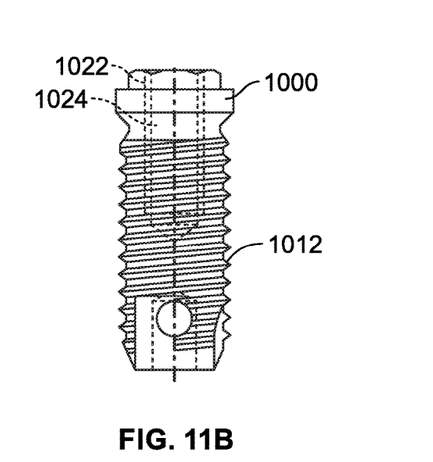

FIG. 11B shows the dental implant 1000 with the temporary abutment 1010 removed. The dental tool 100 is used to resurface the threads 1012 and remove debris before a new mating component is inserted on the implant 1000.

Figure 11C:
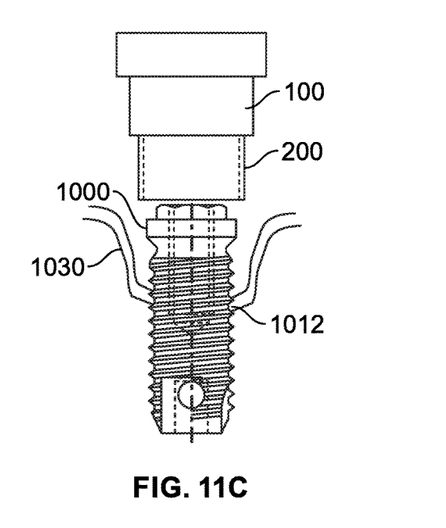
Figure 11D:
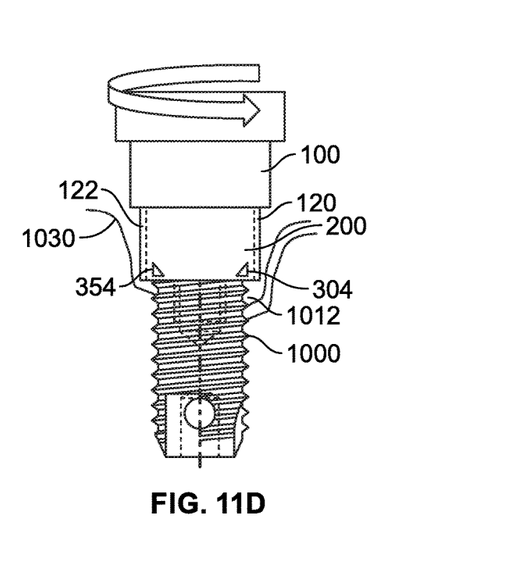

FIG. 11C shows the implant 1000 inserted in the bone 1030. As shown in FIG. 11C, parts of the threads 1012 over the bone 1030 are exposed and thus vulnerable to debris and bacteria. The dental tool 100 is positioned over the implant 1000 with the compression sleeve 112 in an open position. As shown in FIG. 11D, the socket member 200 of the dental tool 100 is positioned so the heads 304 and 354 of the blades 120 and 122 engage the threads 1012. The dental tool 100 is then rotated in a clockwise direction to the base of the level of the bone 1030. The rotation of the dental tool 100 is performed by engaging a wrench with the connection member 260 of the support cylinder 210. The compression sleeve 112 is then moved down to the closed position. The dental tool 100 is then rotated in a counter-clockwise direction to move the dental tool 100 away from the level of the bone 1030. In the rotation of the tool 100, the heads 304 and 354 of the blades 120 and 122 traverse the threads 1012 and thereby clean and resurface the threads 1012.

Figure 12:
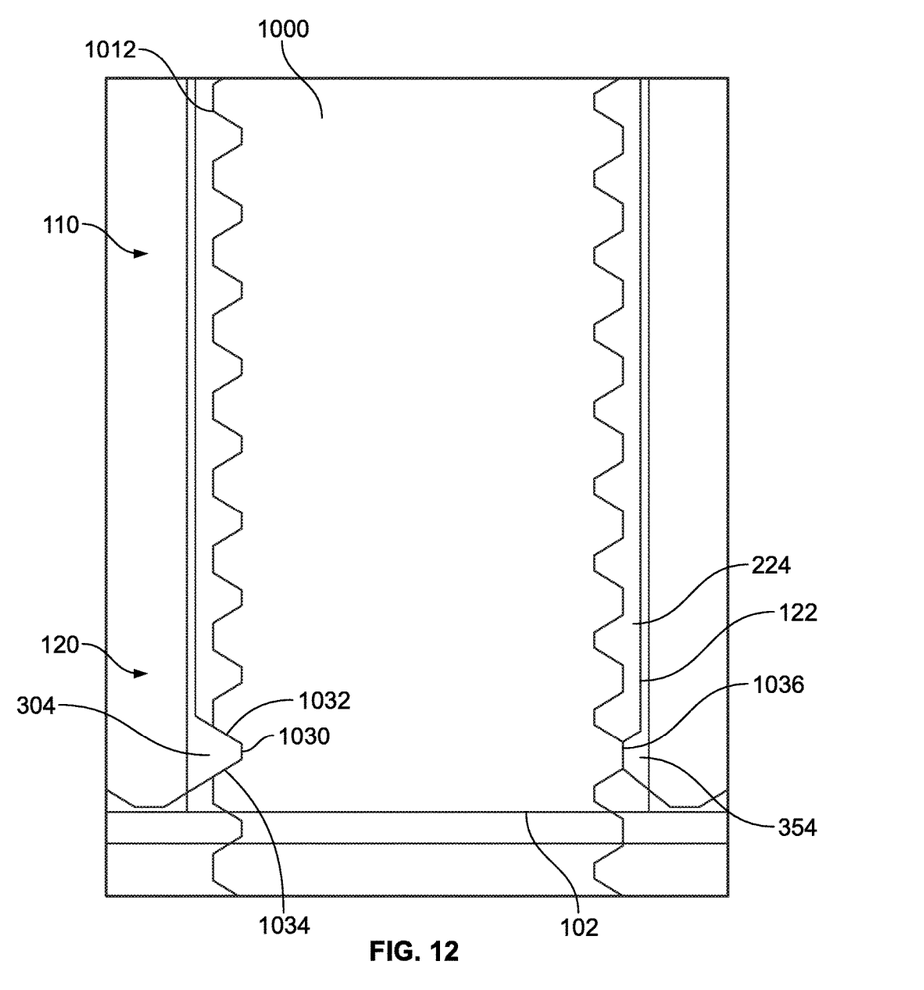
FIG. 12 is a close-up cross-section view of the heads of the blades of the dental tool in FIG. 1 interfacing with the thread forms of an implant.

FIG. 12 shows the interaction between the heads 304 and 354 of the blades 120 and 122 and the threads 1012 of the implant 1000. Each head 304 and 354 of the blades 120 and 122 is positioned on or behind center respective to cutting direction allowing blade to cut efficiently and effectively. Thus, the cutting face of the heads 304 and 354 are at the height of the diameter of the thread allowing relief during cutting. As shown in FIG. 12, the head 354 of the blade 122 contacts a minor aspect 1030 and flanks 1032 and 1034 of the thread 1012 of the implant 1000. The contact of the head 304 scrapes away the material allowing resurfacing of the minor aspect 1030 and flanks 1032 and 1034. The head 304 cleans away debris when the head 304 is rotated relative to the major aspect 1030 of the thread 1012. The head 354 of the blade 122 contacts a major aspect 1036 of the thread 1012 of the implant 1000. The contact of the head 354 scrapes away the material allowing resurfacing of the major aspect 1036. The head 354 cleans away debris when the head 304 is rotated relative to the major aspect 1036 of the thread 1112.

The assembly of the blades 120 and 122, main body 110 and sleeve 112 are designed to cut and contain debris and material while working from bone/implant base upward in a counter clockwise rotation away from the bone 1030. The dental tool 100 thus resurfaces the thread surfaces of the implant 1000 rather than simply cleaning or debriding them. The heads 304 and 354 of the blades 120 and 122 actually cut the implant material creating a new implantoplasty surface desirable for bone grafting.

The form of the heads 304 and 354 of the blades 120 and 122 is designed to be slightly larger in width, depth, and angle than the threads 1012. The larger dimensions of the heads 304 and 354 while engaged into the implant thread 1012, and under pressure from the closed sleeve 112, force the cutter to lay slightly back causing a compound angle. This also causes a conforming compression against the thread form of the threads 1012, allowing an ever deepening cut if necessary. This allows the user to engage the dental tool 100 and use multiple rotational motions up and down the implant 1000 to deepen the cut if it is desired to further remove the material of the implant 1000.

The example dental tool 100 is designed so all aspects of the implant thread geometry are cut simultaneously within one rotational pass of the dental tool 100. Thus, the thread root, thread flank, and thread crest of the thread form are cut by the dental tool 100. The example dental tool 100 is designed so the blades 120 and 122 can be rigid no matter the length of the thread of the dental implant to be cut. In this example, the working length of the dental tool 100 is about 10 mm, although a longer working length of the dental tool 100 may be provided using the principles described herein.

As explained above, the blades 120 and 122 of the dental tool 100 are not fixed to the main body 110. The blades 120 and 122 are captured within the assembly with the main body 110 and the compression sleeve 112 allowing the blades 120 and 122 to pivot to maneuver over the implant 1000 when the sleeve 112 is drawn to the closed position to hold the blades 120 and 122.

The example dental tool 100 allows thorough cleaning and resurfacing of all aspects of the thread form of a dental implant such as the implant 1000 in FIGS. 11-12. These aspects include minor, major and flank aspects as well as all surfaces of the thread form. The example dental tool 100 allows the ability to cut deep in the implant surface due to rigid compression to provide a complete new surface which is key to implantoplasty success. The example dental tool 100 provides cleaned new surfaces within minutes rather than hours of chair time. The example dental tool 100 retains debris instead of dispersing debris throughout the implant site. The example dental tool 100 also provides an option to save a failing implant site rather than requiring a replacement thus saving the need for additional prosthetic work.

The example dental tool 100 may be designed and built to interact with various thread forms and be specific to all makes and models of threaded dental implants. The utilization of the example dental tool 100 can interrupt the onset of peri-implantitis by resurfacing the implant thread form. This allows for successful bone grafting and ensures of the implants response to the grafted site. This allows the continued utilization of the existing prosthetics which are built to the existing implant's position. This creates a savings of thousands of dollars by using the existing implant rather than removal and replacement, scrapping the prosthetics mentioned.

The terminology used herein is for the purpose of describing particular embodiments only, and is not intended to be limiting of the invention. As used herein, the singular forms "a," "an" and "the" are intended to include the plural forms as well, unless the context clearly indicates otherwise. Furthermore, to the extent that the terms "including", "includes," "having," "has," "with," or variants thereof, are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art. Furthermore terms, such as those defined in commonly used dictionaries, should be interpreted as having a meaning that is consistent with their meaning in the context of the relevant art, and will not be interpreted in an idealized or overly formal sense unless expressly so defined herein.

While various embodiments of the present invention have been described above, it should be understood that they have been presented by way of example only, and not limitation. Numerous changes to the disclosed embodiments can be made in accordance with the disclosure herein, without departing from the spirit or scope of the invention. Thus, the breadth and scope of the present invention should not be limited by any of the above described embodiments. Rather, the scope of the invention should be defined in accordance with the following claims and their equivalents.

What is claimed is:

1. A dental tool for resurfacing thread forms of a dental implant, the tool comprising:
   a main body having a cylindrical member with a slot;
   a blade having a lateral support member having an inner surface and an outer surface, and a head extending from one end of the inner surface, the support member of the blade inserted in the slot to orient the head to protrude from an interior surface of the cylindrical member of the main body, wherein the outer surface is flush with an exterior surface of cylindrical member and the inner surface is flush with the interior surface of the cylindrical member when the support member is inserted in the slot, and wherein the main body may be rotated into traversing a thread form of the implant; and
   a compression sleeve inserted over the exterior surface of the main body, the compression sleeve having an open position and a closed position to hold the blade in the slot.

2. The dental tool of claim 1, further comprising a second blade including a second head, wherein the second blade is inserted in a second slot in the main body, the second head oriented to protrude from the interior surface of the cylindrical member of the main body.

3. The dental tool of claim 1, wherein the head of the blade is shaped to allow the blade to resurface a major diameter of the thread form.

4. The dental tool of claim 2, wherein the second head of the second blade is shaped to resurface the minor and flank aspects of the thread form.

5. The dental tool of claim 1, wherein the main body is fabricated from a thermoplastic material and the blade and compression sleeve are fabricated from a metal material.

6. The dental tool of claim 1, wherein the main body includes a connection member that has a shape that may be mated with a wrench to rotate the main body.

7. The dental tool of claim 1, further comprising a containment pin inserted in the main body to define the open position of the compression sleeve.

8. A method of resurfacing the thread form of a dental implant seated in bone, the method comprising:
   inserting a dental tool over the dental implant, the dental tool including a main body having a cylindrical member with a slot, a blade having a head, the blade inserted in the slot to orient the head to protrude from the interior surface of the main body and a compression sleeve located over the main body, the compression sleeve having an open position and a closed position to hold the blade in the slot;
   rotating the dental tool in a first rotational direction to contact the bone;
   moving the compression sleeve from the open position to the closed position; and rotating the dental tool in a second rotational direction to resurface the thread form of the dental implant by contact between the head and the thread form.

9. The method of claim 8, wherein the dental tool includes a second blade including a second head, wherein the second blade is inserted in a second slot in the cylindrical member of the main body, the second head oriented to protrude from the interior surface of the cylindrical member of the main body.

10. The method of claim 8, wherein the head of the blade is shaped to allow the blade to resurface a major diameter of the thread form.

11. The method of claim 9, wherein the second head of the second blade is shaped to resurface the minor and flank aspects of the thread form.

12. The method of claim 8, wherein the main body is fabricated from a thermoplastic material and the blade and compression sleeve are fabricated from a metal material.

13. The method of claim 8, wherein the main body includes a connection member that has a shape, and wherein the rotations of the dental tool are performed by a wrench connected to the connection member.

14. The method of claim 8, wherein the dental tool includes a containment pin insertable in the main body to define the open position of the compression sleeve.

* * * * *